United States Patent [19]

Koenig et al.

[11] 4,297,300

[45] Oct. 27, 1981

[54] NOVEL α-HALOALKYLCARBAMIC ACID HALIDES, AND A PROCESS FOR THE PREPARATION OF α-HALOALKYLCARBAMIC ACID HALIDES

[75] Inventors: Karl-Heinz Koenig, Frankenthal; Karl-Heinz Feuerherd, Ludwigshafen, both of Fed. Rep. of Germany

[73] Assignee: BASF Aktiengesellschaft, Fed. Rep. of Germany

[21] Appl. No.: 51,744

[22] Filed: Jun. 25, 1979

[30] Foreign Application Priority Data

Jul. 14, 1978 [DE] Fed. Rep. of Germany ....... 2830969

[51] Int. Cl.$^3$ ............................................. C07C 53/50
[52] U.S. Cl. ................................................. 260/544 C
[58] Field of Search ..................................... 260/544 C

[56] References Cited

U.S. PATENT DOCUMENTS

| | | | |
|---|---|---|---|
| 3,468,923 | 9/1969 | Koenig et al. | 260/544 C |
| 4,137,261 | 1/1979 | Koenig et al. | 260/544 C |
| 4,189,446 | 2/1980 | Koenig et al. | 424/315 |

FOREIGN PATENT DOCUMENTS 763948 7/1967 Canada.

OTHER PUBLICATIONS

Royals, E. Earl "Advanced Organic Chemistry" Prentice-Hall, Publ. (1963) pp. 361–364.

*Primary Examiner*—Natalie Trousof
*Assistant Examiner*—L. Hendriksen
*Attorney, Agent, or Firm*—Keil & Witherspoon

[57] ABSTRACT

Novel α-haloalkylcarbamic acid halides, and a process for the preparation of α-haloalkylcarbamic acid halides by reacting alkenyl isocyanates with hydrogen halide. The α-haloalkylcarbamic acid halides obtained by the process of the invention are valuable starting materials for the preparation of surface-coating raw materials, textile coating agents, dyes, drugs and crop protection agents.

1 Claim, No Drawings

NOVEL α-HALOALKYLCARBAMIC ACID HALIDES, AND A PROCESS FOR THE PREPARATION OF α-HALOALKYLCARBAMIC ACID HALIDES

The present invention relates to novel α-haloalkylcarbamic acid halides and to a process for the preparation of α-haloalkylcarbamic acid halides by reaction of an alkenyl isocyanate with a hydrogen halide.

Angewandte Chemie, 74 (1962), 848–855 discloses that an alkylcarbamic acid chloride can be reacted with elementary chlorine to give a mixture of a chloroalkylcarbamic acid chloride and polychlorinated products. However, the mixtures obtained are difficult to separate both in respect of the degree of halogenation and of the position of the halogen entering the molecule. The process is unsatisfactory in respect of yield and purity of the end product and in respect of simplicity and economy of operation, and defined individual compounds, in particular mono-α-haloalkylcarbamyl chlorides, cannot be isolated in substantial amount.

We have found that an α-haloalkylcarbamic acid halide of the formula

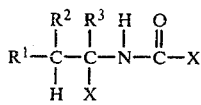

where $R^1$, $R^2$ and $R^3$ may be identical or different and each is an aliphatic, cycloaliphatic, araliphatic, aliphaticaromatic or aromatic radical, $R^1$ and $R^2$ together with the adjoining carbon, or $R^2$ and $R^3$ together with the two adjoining carbons, may also be members of an alicyclic ring, one or two of $R^1$, $R^2$ and $R^3$ may also be hydrogen and X is halogen, is obtained in an advantageous manner if an alkenyl isocyanate of the formula

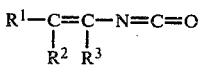

where $R^1$, $R^2$ and $R^3$ have the above meanings, is reacted with a hydrogen halide at from −78° C. to +80° C.

Further, we have found the novel α-haloalkylcarbamic acid halides of the formula

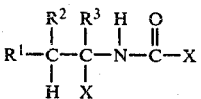

where $R^1$, $R^2$ and $R^3$ may be identical or different and each is alkyl of 1 to 12 carbon atoms, cycloalkyl of 5 or 6 carbon atoms, aralkyl or alkylaryl of 7 to 12 carbon atoms or phenyl, $R^1$ and $R^2$ together with the adjoining carbon or $R^2$ and $R^3$ together with the two adjoining carbons may also be members of an alicyclic ring, one or two of $R^1$, $R^2$ and $R^3$ may also be hydrogen, X is halogen and, if $R^2$ and $R^3$ are both hydrogen, $R^1$ is a cycloaliphatic, araliphatic, aliphatic-aromatic or aromatic radical.

When using hydrogen chloride and but-1-enyl isocyanate, the reaction can be represented by the following equation:

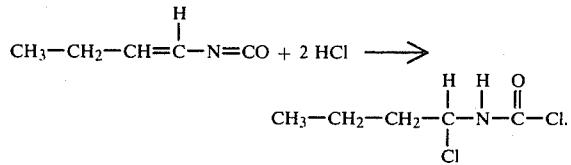

Compared to the conventional process, the process according to the invention gives α-haloalkylcarbamic acid halides more simply and more economically and in better yield and higher purity. Working-up is substantially simpler since, instead of a reaction mixture containing a large number of components, defined end products are obtained. All these advantageous results are surprising since, in view of the very reactive starting materials used, the formation of a variety of reaction products was to be expected. Further, it was to be expected that α,β-unsaturated nitrogen compounds would very easily polymerize or hydrolyze under the action of acids. For example, even small amounts of an inorganic acid convert N-vinlypyrrolidone into a mixture of oligomers (Ullmanns Encyklopädie der technischen Chemie, volume 14, page 261). Bull. Soc. Chim. Belg., 65 (1956), 291–296 shows that vinyl isocyanate is hydrolyzed to acetaldehyde by aqueous 12 N hydrochloric acid in acetone.

The starting materials can be prepared, for example, by reacting an appropriately substituted acrylic acid halide with sodium azide (Bull. Soc. Chim. Belg., loc. cit.) or by thermally decomposing a N-tert.-butyl-N-alkenylcarbamic acid halide. The hydrogen halide, advantageously hydrogen iodide, preferably hydrogen bromide and in particular hydrogen chloride, is used in the stoichiometric amount or in excess, preferably in an amount of from 2 to 2.2 moles of hydrogen halide per mole of starting material II.

Preferred starting materials II and accordingly preferred products I are those where $R^1$, $R^2$ and $R^3$ may be identical or different and each is alkyl of 1 to 12 carbon atoms, cycloalkyl of 5 or 6 carbon atoms, aralkyl or alkylaryl of 7 to 12 carbon atoms or phenyl, $R^1$ and $R^2$ together with the adjoining carbon or $R^2$ and $R^3$ together with the two adjoining carbons may also be members of a monocyclic or bicyclic, alicyclic ring of 5 to 9 carbon atoms and one or two of the radicals $R^1$, $R^2$ and $R^3$ can also be hydrogen. The above radicals and rings may in addition be substituted by groups which are inert under the reaction conditions, for example alkyl of 1 to 4 carbon atoms.

The following alkenyl isocyanates are examples of suitable starting materials II: propenyl, butenyl, pentenyl, hexenyl, heptenyl, ocetnyl, nonenyl, decenyl, undecenyl, dodecenyl, 2-methylpropenyl, 2-methylbutenyl, 2-methylpentenyl, 2-methylhexenyl, 2-methylheptenyl, 2-methyloctenyl, 2-methylnonenyl, 2-methyldecenyl, 2-methylundecenyl, 2-methyldodecenyl, 2-ethylbutenyl, 2-ethylpentenyl, 2-ethylhexenyl, 2-ethylheptenyl, 2-ethyloctenyl, 2-ethylnonenyl, 2-ethyldecenyl, 2-ethylundecenyl, 2-ethyldodecenyl, 1,2-dimethylvinyl, 1,2-dimethylpropenyl, 1,2-dimethylbutenyl, 1,2-dimethylpentenyl, 1,2-dimethylhexenyl, 1,2-dimethylheptenyl, 1,2-dimethyloctenyl, 1,2-dimethylnonenyl, 3-methylbutenyl, 3-methylpentenyl, 3-methylhexenyl, 3-methylheptenyl, 3-methyloctenyl, 3-methylnonenyl, 3-methyldecenyl, 3-methylundecenyl, 3-methyldodecenyl, cyclohexylidenemethyl, phenylvinyl, benzylvinyl, (4-methylphenyl)-vinyl, cyclohexylvinyl, cyclohex-1-en-1-yl, (2′-norbornylidene)-methyl and norbornen-2-yl isocyanate.

The reaction can be carried out at from +80° C. to −78° C., but is in general carried out at from +40° C. to −78° C., preferably from +30° to −78° C., in particular from 0° to −40° C., under atmospheric or superatmospheric pressure, preferably at from 0.7 to 2 bar, continuously or batchwise. It can be carried out without a solvent, but advantageously a solvent which is inert under the reaction conditions is used. Water is not used. Solvents which can serve as the reaction medium for further conversions of the end product, especially of the α-chloroalkylcarbamic acid chlorides, are preferred. Examples of suitable solvents are aromatic hydrocarbons, eg. toluene, ethylbenzene, o-, m- and p-xylene, isopropylbenzene and methylnaphthalene, halohydrocarbons, especially chlorohydrocarbons, eg. tetrachloroethylene, 1,1,2,2- or 1,1,2,2-tetrachloroethane, amyl chloride, cyclohexyl chloride, 1,2-dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- or 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and β,β′dichlorodiethyl ether; ketones, eg. methyl ethy ketone, acetone, diisopropl ketone, diethyl ketone, methyl isobutyl ketone, acetophenone, cyclohexanone, ethyl isoamyl ketone, diisobutyl ketone, methylcyclohexanone and dimethylcyclohexanone; ester, eg. methyl acetate, n-propyl acetate, methyl propionate, butyl acetate, ethyl formate, methyl phthalate, methyl benzoate, ethyl acetate and phenyl acetate; aliphatic and cycloaliphatic hydrocarbons, eg. pentane, heptane, pinane, nonane, gasoline fractions within a boiling range of from 70° to 190° C., cyclohexane, methylcyclohexane, decalin, naphtha, hexane, ligroin, 2,2,4-trimethylpentane, 2,2,3-trimethylpentane, 2,3,3-trimethylpentane and octane; and mixtures of the above. Advantageously, the solvent is used in an amount of from 200 to 10,000 percent by weight, preferably from 300 to 2,000 percent by weight, based on starting material II.

The reaction may be carried out as follows: a mixture of the starting materials, advantageously together with a solvent, is kept at the reaction temperature for from 0.1 to 4 hours. Advantageously, the starting material II is first introduced into the solvent and the hydrogen halide is passed in at the reaction temperature. In the case of the α-iodoalkylcarbamic acid iodides it is advantageous, however, to mix the hydrogen iodide and solvent and then add the starting material II slowly. Stirring of the reaction solution is advantageously continued for an additionl 0.25 to one hour. The end product is then isolated from the mixture in the conventional manner, for example by crystallization and filtration.

The α-haloalkylcarbamic acid halides prepared by the process of the invention are valuable starting materials for the preparation of surface-coating raw materials, textile coating agents, dyes, drugs and crop protection agents. The novel compounds, especially those of the formula I in which $R^1$, $R^2$ and $R^3$ have the preferred meanings mentioned above, in particular α-chloropropylcarbamic acid chloride, α-chlorobutylcarbamic acid chloride, α-chloropentylcarbamic acid chloride, α-chlorohexylcarbamic acid chloride, α-chloroheptylcarbamic acid chloride, α-chlorooctylcarbamic chloride, α-chlorononylcarbamic acid chloride, α-chlorodecylcarbamic acid chloride, α-chloroundecylcarbamic acid chloride, α-chlorododecylcarbamic acid chloride, α-bromopropylcarbamic acid bromide, α-bromobutylcarbamic acid bromide, α-bromopentylcarbamic acid bromide, α-bromohexylcarbamic acid bromide, α-bromoheptylcarbamic acid bromide, α-bromooctylcarbamic acid bromide, α-bromononylcarbamic acid bromide, α-bromodecylcarbamic acid bromide, α-bromoundecylcarbamic acid bromide, α-bromododecylcarbamic acid bromide, 1-chloro-2-methyl-propylcarbamic acid chloride, 1-bromo-1-methyl-propylcarbamic acid bromide, 1-chloro-2-methyl-butylcarbamic acid chloride, 1-bromo-2-methyl-butylcarbamic acid bromide, 1-chloro-2-methyl-pentylcarbamic acid chloride, 1-bromo-2-methyl-pentylcarbamic acid bromide, 1-chloro-2-methyl-hexylcarbamic acid chloride, 1-bromo-2-methyl-hexylcarbamic acid bromide, 1-chloro-2-methyl-heptylcarbamic acid chloride, 1-bromo-2-methyl-heptylcarbamic acid bromide, 1-chloro-2-methyl-octylcarbamic acid chloride, 1-bromo-2-methyl-octylcarbamic acid bromide, 1-chloro-2-methyl-nonylcarbamic acid chloride, 1-bromo-2-methyl-nonylcarbamic acid bromide, 1-chloro-2-methyl-decylcarbamic acid chloride, 1-bromo-2-methyl-decylcarbamic acid bromide, 1-chloro-2-methyl-undecylcarbamic acid chloride, 1-bromo-2-methyl-undecylcarbamic acid bromide, 1-chloro-1-ethyl-butylcarbamic acid chloride, 1-bromo-1-ethyl-butylcarbamic acid bromide, 1-chloro-2-ethyl-pentylcarbamic acid chloride, 1-bromo-2-ethyl-pentylcarbamic acid bromide, 1-chloro-2-ethyl-hexylcarbamic acid chloride, 1-bromo-2-ethyl-hexylcarbamic acid bromide, 1-chloro-3-methyl-butylcarbamic acid chloride, 1-bromo-3-methyl-butylcarbamic acid bromide, 1-chloro-3-methyl-pentylcarbamic acid chloride, 1-bromo-3-methyl-pentylcarbamic acid bromide, 1-chloro-3-methyl-hexylcarbamic acid chloride, 1-bromo-3-methyl-hexylcarbamic acid bromide, 1-chloro-1-(cyclohexyl)-methylcarbamic acid chloride, 1-bromo-1-(cyclohexyl)-methylcarbamic acid bromide, 1-chloro-2-phenyl-ethylcarbamic acid chloride, 1-bromo-2-phenyl-ethylcarbamic acid bromide, 1-chloro-2-phenyl-propylcarbamic acid chloride, 1-bromo-2-phenyl-propylcarbamic acid bromide, chloro-(norborn-2-yl)-methylcarbamic acid chloride and bromo-(norborn-2-yl)-methylcarbamic acid bromide are advantageous compounds for the above uses. The α-monohaloalkylcarbamic acid chlorides according to the invention are valuable intermediates for α,β,-unsaturated isocyanates and α,β-unsaturated carbamic acid chlorides. These, for example vinyl isocyanate or propenyl isocyanate, are interesting monomers for further industrial syntheses.

In the Examples, parts are by weight.

EXAMPLE 1

22 parts of 3-methylbut-1-enyl isocyanate are introduced into 75 parts of methylene chloride, and 15 parts of hydrogen chloride are passed into this solution in the course of 40 minutes at −39° C. The reaction solution is then stirred for a further 20 minutes at the same temperature. After filtration, 30 parts (82% of theory) of 1-chloro-3-methyl-butylcarbamic acid chloride of melting point 35° C. are obtained; the NMR spectrum in $CDCl_3$ (with tetramethylsilane as the standard) shows the following:

| | |
|---|---|
| $(CH_3-)$ | 0.9 ppm |
| $(-CH-CH_2-)$ | 1.7–1.9 ppm |
| $(Cl-C-H)$ | 5.6 ppm |
| $(NH)$ | 6.5 ppm |

EXAMPLE 2

21 parts of cyclohexylidenemethyl isocyanate are introduced into 80 parts of methylene chloride, and 8 parts of hydrogen chloride are passed into this solution in the course of 30 minutes at −39° C. The reaction solution is then stirred for a further 45 minutes at the same temperature. After stripping off the solvent at −20° C., 31 parts (96% of theory) of liquid chloro-(cyclohexyl)-methylcarbamic acid chloride are obtained. NMR spectrum in $CDCl_3$ (with tetramethylsilane as the standard):

| | |
|---|---|
| $(C_6H_{11}-CH_2-)$ | 1–2 ppm |
| $(Cl-C-H)$ | 5.5 ppm |
| $(NH)$ | 6.5 ppm |

EXAMPLE 3

80 parts of but-1-enyl isocyanate are introduced into 400 parts of chloroform. 62 parts of hydrogen chloride are passed into the solution in the course of 1.5 hours at −30° C. The reaction solution is then stirred for a further 30 minutes at −20° C. After filtration, 128 parts (91% of theory) of α-chlorobutylcarbamic acid chloride of melting point 5°–10° C. are obtained; the NMR spectrum in $CDCl_3$ (with tetramethylsilane as the standard) shows the following:

| | |
|---|---|
| $(CH_3)$ | 0.9 ppm |
| $(-CH_2-)$ | 1.4–1.6 ppm |
| $(Cl-CH)$ | 5.7 ppm |
| $(NH)$ | 6.6 ppm |

EXAMPLE 4

54 parts of prop-1-enyl isocyanate are introduced into 200 parts of carbon tetrachloride. 105 parts of hydrogen bromide are passed into the solution in the course of 50 minutes at −20° C. The reaction solution is then stirred for a further 60 minutes at −20° C. After filtration, 139 parts (86% of theory) of liquid α-bromopropylcarbamic acid bromide are obtained. NMR spectrum in $CDCl_3$ (with tetramethylsilane as the standard):

| | |
|---|---|
| $(CH_3)$ | 1.0 ppm |
| $(-CH_2-)$ | 1.7 ppm |
| $(Br-C-H)$ | 5.8 ppm |
| $(NH)$ | 6.5 ppm |

EXAMPLE 5

80 parts of hydrogen iodide are introduced into 130 parts of chloroform at −50° C. 25 parts of 1-propenyl isocyanate are added slowly to this solution in the course of 40 minutes. The reaction solution is then stirred for a further 20 minutes at −50° C. After filtration, 78 parts (77% of theory) of α-iodopropylcarbamic acid iodide, having a decomposition point at 10° C., are obtained; the NMR spectrum in $CDCl_3$ (with tetramethylsilane as the standard) shows the following:

| | |
|---|---|
| $(-CH_3)$ | 1.0 ppm |
| $(-CH_2-)$ | 2.1 ppm |
| $(I-CH)$ | 5.9 ppm |
| $(NH)$ | 7.1 ppm |

EXAMPLES 6 to 10

The following end products I are prepared similarly to Example 4 in respect of the amount of starting material II and its molar ratio to the hydrogen halide used and in respect of the reaction conditions and working-up conditions:

| Example | | $^1$H—NMR spectrum ($CDCl_3$) δ(ppm) | | Yield in % of theory |
|---|---|---|---|---|
| 6 | 1-Chloropropyl-carbamic acid chloride | 1.1<br>2.0<br>5.6<br>6.8 | (3)t<br>(2)p<br>(1)d,t<br>(1)broad | 97 |
| 7 | 1-Bromobutyl-carbamic acid bromide | 0.9<br>1.4<br>1.9<br>5.7<br>6.5 | (3)t<br>(2)m<br>(2)m<br>(1)m<br>(1)broad | 95 |
| 8 | 1-Bromo-2-methyl-butylcarbamic acid bromide | 1.0<br>1.4–2.0<br>5.9<br>6.5 | (6)t<br>(3)m<br>(1)d,d<br>(1)broad | 86 |
| 9 | 1-Bromooctyl-carbamic acid bromide | 0.9<br>1.3<br>2.1<br>5.8<br>6.9 | (3)t<br>(10)s,broad<br>(2)m<br>(1)m<br>(1)broad | 94 |
| 10 | 1-Bromo-2-phenyl-propylcarbamic acid bromide | 2.0<br>3.3<br>6.2<br>6.85<br>7.3 | (3)s<br>(1)m<br>(1)m<br>(1)broad<br>(5)s | 88 |

EXAMPLE 11

The following end product I is prepared similarly to Example 5 in respect of the amount of starting material II and its molar ratio to the hydrogen halide used and in respect of the reaction conditions and work-up conditions:

|  | $^1$H-NMR spectrum (CDCl$_3$) | δ(ppm) | Yield of % of theory |
| --- | --- | --- | --- |
| 1-Iodobutylcarbamic acid iodide | 1.0 | (3)t | 83 |
|  | 1.5 | (2)m |  |
|  | 2.0 | (2)m |  |
|  | 6.0 | (1)m |  |
|  | 6.5 | (1)broad |  |

We claim:
1. An α-haloalkylcarbamic acid halide of the formula

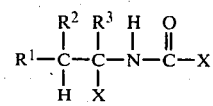

where $R^1$, $R^2$ and $R^3$ may be identical or different and each is cycloalkyl of 5 or 6 carbon atoms, $R^1$ and $R^2$ together with the adjoining carbon or $R^2$ and $R^3$ together with the two adjoining carbons may also be members of a monocyclic or bicyclic alicyclic ring of 5 to 9 carbon atoms, one or two of $R^1$, $R^2$ and $R^3$ may also be hydrogen, and X is halogen.

* * * * *